(12) United States Patent
Horie

(10) Patent No.: US 8,142,517 B2
(45) Date of Patent: Mar. 27, 2012

(54) PROSTHESIS

(76) Inventor: Kota Horie, Minokamo (JP)

( * ) Notice: Subject to any disclaimer, the term of this patent is extended or adjusted under 35 U.S.C. 154(b) by 173 days.

(21) Appl. No.: 12/497,117

(22) Filed: Jul. 2, 2009

(65) Prior Publication Data

US 2010/0004756 A1    Jan. 7, 2010

(30) Foreign Application Priority Data

Jul. 7, 2008    (JP) ................................ 2008-176467

(51) Int. Cl.
*A61F 2/80*    (2006.01)
(52) U.S. Cl. ........................................................ 623/36
(58) Field of Classification Search ............... 623/32–37
See application file for complete search history.

(56) References Cited

U.S. PATENT DOCUMENTS

| | | | | |
|---|---|---|---|---|
| 2004/0143345 A1* | 7/2004 | Caspers | ........................... | 623/36 |
| 2007/0264482 A1* | 11/2007 | Banker et al. | ................. | 428/223 |
| 2010/0327619 A1* | 12/2010 | Schmeichel et al. | ..... | 296/100.16 |

* cited by examiner

*Primary Examiner* — Bruce E Snow

(74) *Attorney, Agent, or Firm* — Schwegman, Lundberg & Woessner, P.A.

(57) ABSTRACT

A prosthesis for attachment to a residual limb. The prosthesis includes a liner into which the residual limb is insertable, a socket into which the liner is insertable, and a fibrous pile fastener arranged on the inner surface of the liner, the outer surface of the liner, and the inner wall of the socket. Fibers extend from the fibrous pile fastener on inner surface of the liner inclined toward a direction in which the residual limb is inserted into the liner. Fibers extend from the fibrous pile fastener on the outer surface of the liner inclined toward a direction reversed from a direction in which the liner is inserted into the socket. Further, fibers extend from the fibrous pile fastener on the inner wall of the socket toward the direction in which the liner is inserted into the socket.

4 Claims, 3 Drawing Sheets

PROSTHESIS

RELATED APPLICATION

This application claims the benefit of priority, under 35 U.S.C. Section 119, to Japanese Patent Application Serial No. 2008-176467, filed on Jul. 7, 2008, which is incorporated herein by reference in its entirety.

BACKGROUND OF THE INVENTION

The present invention relates to a prosthesis, and more particularly, to a fastener for a prosthesis that stably holds a prosthesis on a residual limb.

A prosthesis is used to replace a missing extremity. For example, a prosthetic leg is attached to a residual leg, and a prosthetic arm is attached to a residual arm. There are a wide variety of such prostheses.

FIG. 3 illustrates an example of a typical prosthesis 1 attachable to a residual limb S, which is a leg in this case. The prosthesis 1 includes a liner 2, which is worn on a residual limb S, and a socket 3, which is fitted onto the residual limb S with the liner 2 arranged in between. The liner 2 is formed from a suitable material such as synthetic leather and shaped in conformance with the residual limb S. The socket 3, which includes a hollow portion 3a, is formed from a suitable material such as a fiber reinforced resin and shaped in conformance with the residual limb S. The hollow portion 3a receives the residual limb S with the liner 2 worn thereon.

When using the prosthesis 1, the liner 2 may slip out of the hollow portion 3a of the socket 3 or fall off from the residual limb S. In the prior art, therefore, a fastener such as a belt 4 is arranged on the socket 3 and fastened to a portion above the residual limb S (in this example, the knee). This prevents separation of the prosthesis 1 from the residual limb S.

As described above, in addition to the liner 2 and socket 3, the prosthesis 1 of the prior art requires a discrete fastener such as the belt 4 to prevent separation of the prosthesis 1 from the residual limb S. This makes the structure of the prosthesis 1 complicated. Further, a fastener such as the belt 4 may interfere with movement of the user.

A liner may be secured to a socket by using a fastener including a first fastening piece, which is arranged on a distal end of a liner, and a second fastening piece, which is arranged at the bottom end of the hollow portion of a socket. The first and second fastening pieces are fastened together to secure the distal end of the liner to the bottom end of the hollow portion in the socket. In this case, however, the internal structure of the prosthesis would also be complicated. Further, space for the fastener is necessary at the bottom part of the hollow portion in the socket. However, since the length of the residual limb differs between each person, sufficient space for this fastener may not be available in the hollow portion. For this reason, the versatility of such a structure is low. Additionally, burdensome fastening and unfastening tasks would become necessary when using such a fastener. Moreover, such a fastener pulls the liner toward the bottom end of the hollow portion in the socket. This, in turn, may pull the residual limb and be uncomfortable for the user. If the residual limb is constantly pulled in such a manner, this would result in the flesh at the residual limb being stretched.

One type of a liner is formed from a flexible material such as silicon resin. This liner adheres to the residual limb and the wall of the hollow portion in the socket so that the prosthesis is not separated from the residual limb. By using such a liner, a discrete fastener does not have to be used to prevent separation of the prosthesis from the residual limb. However, this liner adheres to the residual limb. Therefore, the liner may become moist or irritate the residual limb. This is uncomfortable for the user. Further, the residual limb seals the interior of the liner. This may produce unpleasant noise when movements of the user cause air to leak out of the liner. This is also uncomfortable for the user.

SUMMARY OF THE INVENTION

The present invention provides a prosthesis that is comfortable for a user, remains stably held on a residual limb with a simple structure, prevents the residual limb covered by a liner from becoming moist or irritated, and prevents unpleasant noise from being produced by air leakage.

One aspect of the present invention is a prosthesis for attachment to a residual limb. The prosthesis includes an attachment into which the residual limb is insertable. The attachment includes an inner surface and an outer surface. The prosthesis further includes a fibrous pile fastener from which a plurality of fibers extend. The fibrous pile fastener is arranged on at least either one of the inner surface and outer surface of the attachment.

Another aspect of the present invention is a prosthesis for attachment to a residual limb. The prosthesis includes a socket into which the residual limb is insertable. The socket includes an inner wall. The prosthesis further includes a socket fibrous pile fastener from which a plurality of fibers extend. The socket fibrous pile fastener is arranged on the inner wall of the socket. The fibers extending from the socket fibrous pile fastener on the inner wall of the socket are inclined toward a direction in which the residual limb is inserted into the socket.

A further aspect of the present invention is a prosthesis for attachment to a residual limb. The prosthesis includes a liner into which the residual limb is insertable, a socket into which the liner is insertable, and a fibrous pile fastener from which a plurality of fibers extend. The liner includes an inner surface and an outer surface. The socket includes an inner wall. The fibrous pile fastener is arranged on at least one of the inner surface of the liner, the outer surface of the liner, and the inner wall of the socket. The fibers extending from the fibrous pile fastener on the inner surface of the liner are inclined toward a direction in which the residual limb is inserted into the liner. The fibers extending from the fibrous pile fastener on the outer surface of the liner are inclined toward a direction reversed from a direction in which the liner is inserted into the socket. The fibers extending from the fibrous pile fastener on the inner wall of the socket are inclined toward the direction in which the liner is inserted into the socket.

Yet another aspect of the present invention is a liner for use with a prosthesis in which a residual limb is insertable into the liner. The liner includes an inner surface, an outer surface, and a fibrous pile fastener from which a plurality of inclined fibers extend. The fibrous pile faster is arranged on at least either one of the inner surface and the outer surface.

Still a further aspect of the present invention is a fibrous pile fastener for arrangement on a prosthesis liner or a prosthesis socket. The fibrous pile fastener includes a plurality of fibers extending from a surface and inclining in the same direction. The fibers restrict movement of an object when coming into contact with the object. The fibers produce a relatively small resistance acting in a first direction when in contact with the object to allow movement of the object in the first direction, and the fibers produce a relatively high resistance acting in a second direction when in contact with the object to restrict movement of the object in the second direction.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENT

Figure 1:
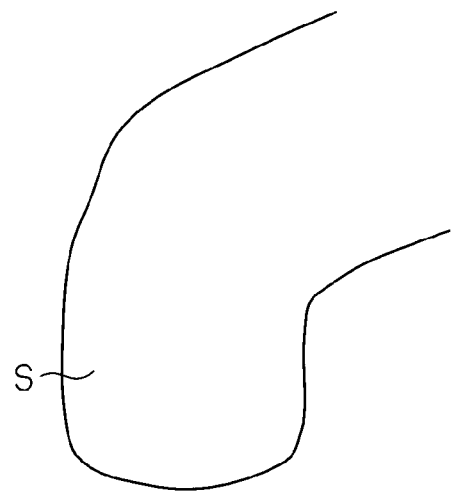
FIG. 1 is a cross-sectional side view showing a preferred embodiment of a prosthesis according to the present invention.
Figure 1:
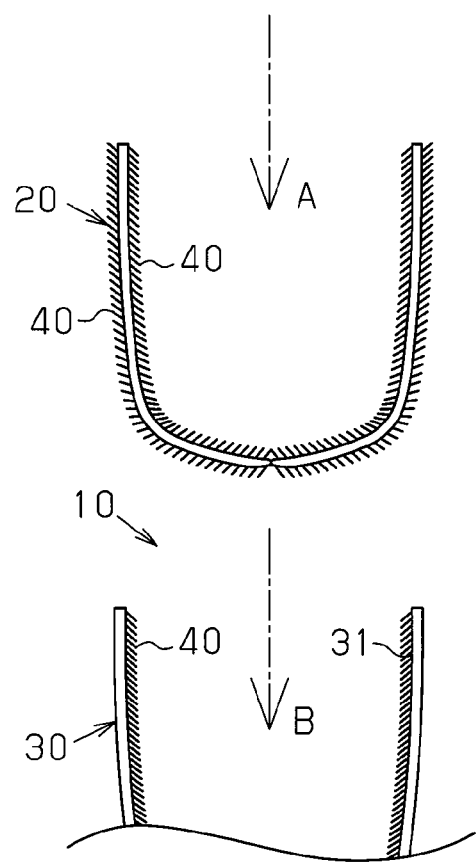

A preferred embodiment of a prosthesis 10 according to the present invention will now be discussed with reference to FIG. 1. In this example, the prosthesis 10 is a prosthetic leg used to replace a leg amputated below the knee. However, the present invention is not limited in such a manner and may be applied to a prosthesis used to replace any appendage including a lower extremity, an upper extremity, and a digit, such as a finger.

The prosthesis 10, which is attachable to a residual limb S, includes a liner 20 and a socket 30. The liner 20 is worn on the residual limb S so as to cover the residual limb S. That is, the residual limn S is inserted into the liner 20. The socket 30, which is formed from a fiber reinforced resin, is attached to the residual limb S with the liner 20 arranged in between. That is, the liner 20 is inserted into the socket 30. Although the socket 30 is not entirely shown in FIG. 1, the socket 30 is shaped in conformance with the user's residual limb S in the same manner as the prior art example shown in FIG. 3. Further, the socket 30 has a hollow portion 31, which is defined by an inner wall and which receives the residual limb S with the liner 20 worn thereon.

Figure 3:
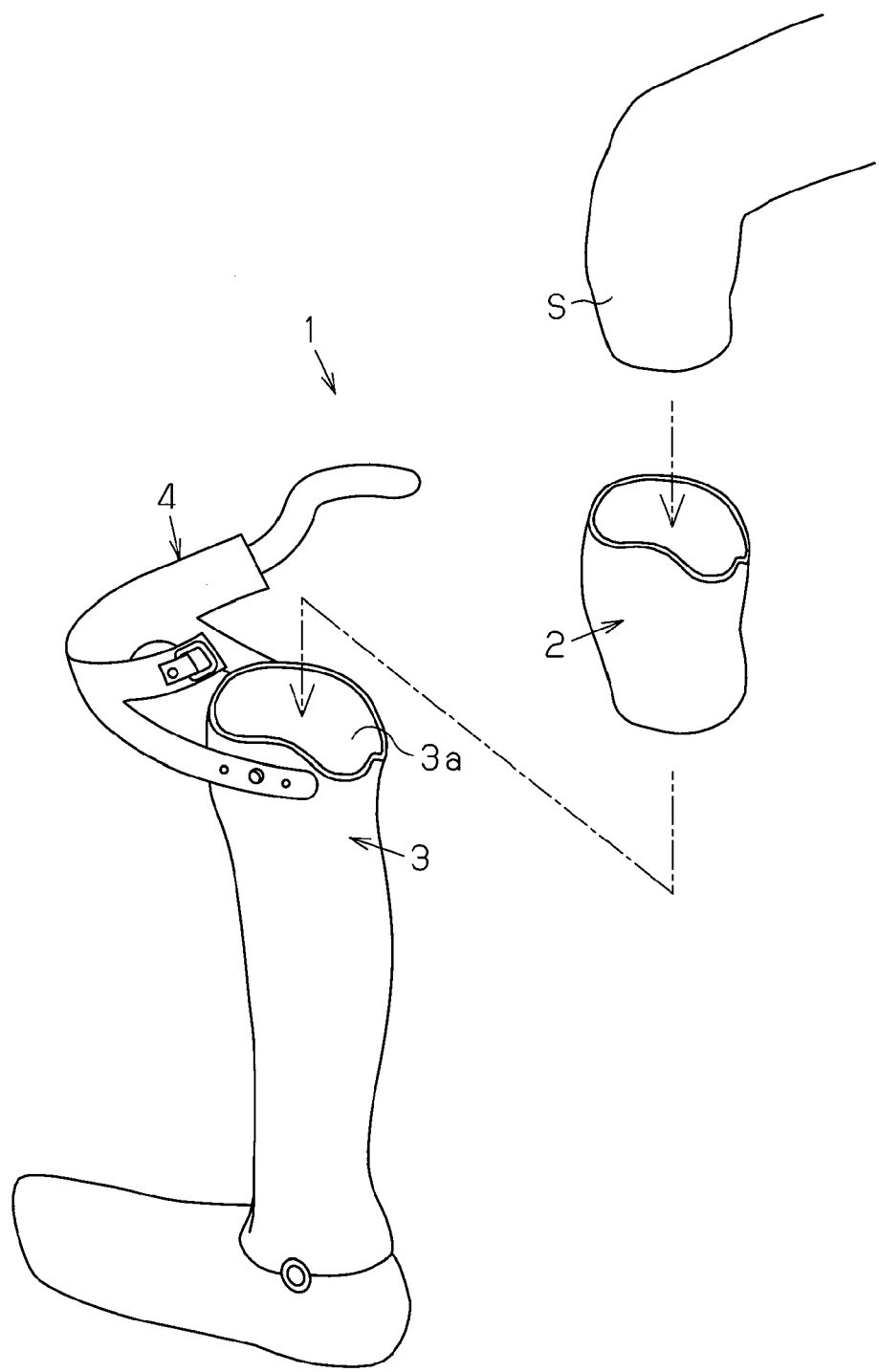
FIG. 3 is a perspective view showing a prior art example of a prosthesis.

The liner 20 overall has a shape similar to that of the prior art example shown in FIG. 3. In this example, the liner 20 is formed from a rubber material containing bubbles such as polychloroprene. The liner 20 is sewn from a rubber material into a shape conforming to the residual limb S of a user.

In this example, the liner 20 is formed from a rubber material having a thickness of two to five millimeters so that the liner 20 elastically deforms in a flexible manner between the residual limb S and the inner wall of the socket 30 even if the shape of the user's residual limb S changes to a certain extent. This keeps the socket 30 properly fitted to the residual limb S. Further, the liner 20, which is formed from a rubber material having a thickness of two millimeters or greater, keeps the residual limb S warm.

In the prosthesis 10 of this example, fibrous pile fasteners 40 are applied to the inner and outer surfaces of the liner 20 and to the inner wall of the socket 30 defining the hollow portion 31. The fibrous pile fasteners 40 each have a surface including fine fibers. Although the fibers of the fibrous pile fasteners 40 are shown in an exaggerated manner in FIG. 1 to facilitate understanding, the fibers actually have a length of one to two millimeters.

In each fibrous pile fastener 40, the fibers extend in substantially the same direction and angle. That is, the fibers are inclined at substantially the same angle relative to the surface of the fibrous pile fastener 40. The fibrous pile fasteners 40 are applied to the inner and outer surfaces of the liner 20 and the inner wall of the socket 30 so that their fibers are inclined in predetermined directions.

More specifically, the fibers extending from the fibrous pile fastener 40 applied to the inner surface of the bag-like liner 20 are inclined toward a direction in which the residual limb S is inserted into the liner 20. In other words, the fibers are inclined toward the direction in which the residual limb S is inserted into the liner 20 (direction of arrow A in FIG. 1). The fibers extending from the fibrous pile fastener 40 applied to the outer surface of the liner 20 are inclined toward a direction reversed from the direction in which the liner 20 is inserted into the socket 30 (direction reversed from the direction of arrow B in FIG. 1). Further, the fibers extending from the fibrous pile fastener 40 applied to the inner wall of the socket 30 are inclined toward a direction in which the liner 20 is inserted into the socket 30 (direction of arrow B in FIG. 1).

Figure 2:
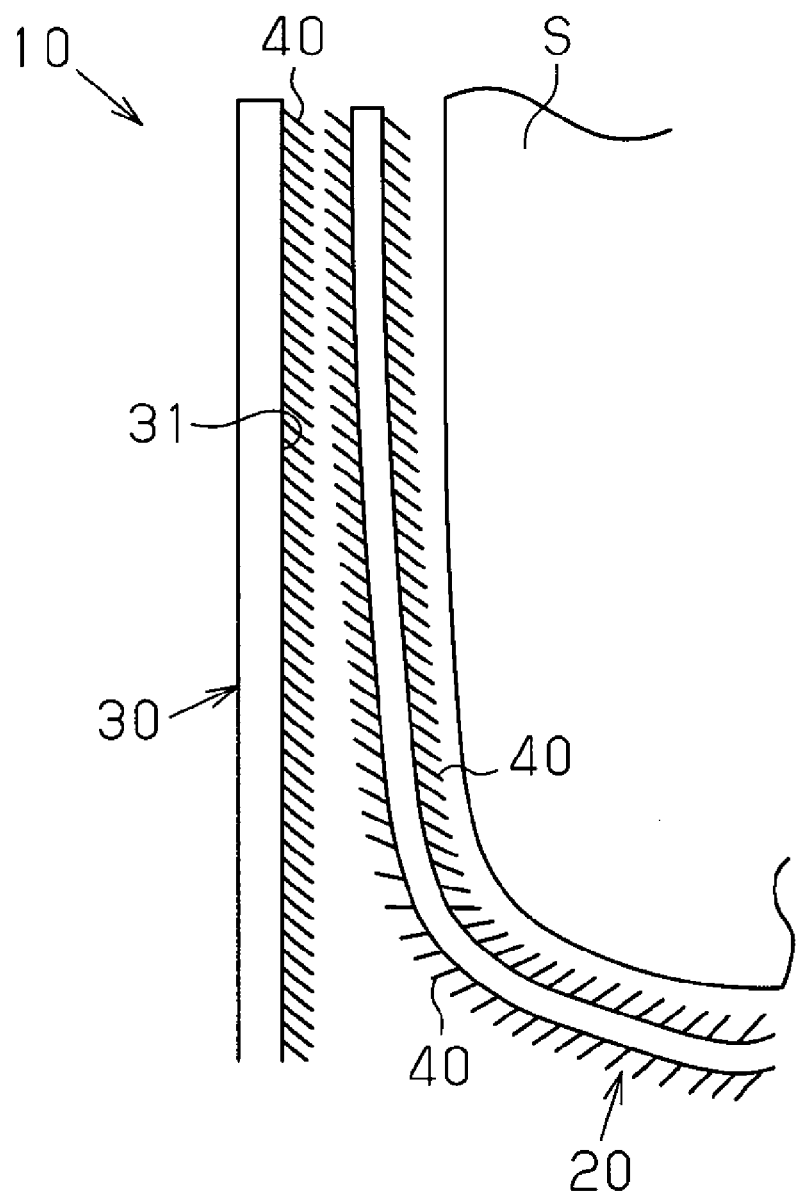
FIG. 2 is a cross-sectional side view showing the prosthesis of FIG. 1 in a state attached to a residual limb.

FIG. 2 shows the prosthesis 10, which includes the fibrous pile fasteners 40 arranged as described above, in a state attached to the residual limb S. In this state, the fibers extending from the fibrous pile fastener 40 on the inner surface of the liner 20 are inclined toward a direction reversed from the direction in which the residual limb S is removed from the liner 20. Thus, the fibers in the fibrous pile fastener 40 on the inner surface of the liner 20 function to resist removal of the liner 20 from the residual limb S. In other words, due to the inclination of the fibers of the fibrous pile fastener 40 on the inner surface of the liner 20, the fibers produce resistance that act to prevent removal of the liner 20 from the residual limb S.

Further, the fibers of the fibrous pile fastener 40 on the outer surface of the liner 20 and the fibers of the fibrous pile fastener 40 on the inner wall of the socket 30 extend in reverse directions and function to resist separation of the liner 20 from the socket 30. Due to the inclination of the fibers of the fibrous pile fastener 40 on the outer surface of the liner 20 and the inclination of the fibers of the fibrous pile fastener 40 on the inner wall of the socket 30, the fibers produce resistance that act to prevent separation of the liner 20 and the socket 30. In this manner, the prosthesis 10 in its entirety resists removal from the residual limb S. Thus, the prosthesis 10 remains stably held on the residual limb S.

When covering the residual limb S with the liner 20, that is, when inserting the residual limb S into the liner 20, the fibers extending from the fibrous pile fastener 40 on the inner surface of the liner 20 are inclined toward the direction in which the residual limb S moves relative to the liner 20. Thus, the fibers of the fibrous pile fastener 40 on the inner surface of the liner 20 do not interfere with the fitting of the liner 20 onto the residual limb S. That is, the liner 20 may be smoothly worn onto the residual limb S since the resistance produced by the fibers is small.

Further, when inserting the liner 20 into the socket 30, the fibers extending from the fibrous pile fastener 40 on the outer surface of the liner 20 are inclined toward the direction in which the socket 30 moves relative to the liner 20. Additionally, the fibers extending from the fibrous pile fastener 40 on the inner wall of the socket 30 are inclined toward the direction in which the liner 20 moves relative to the socket 30. Thus, the fibers of the fibrous pile fastener 40 on the outer surface of the liner 20 and the fibers of the fibrous pile fastener 40 on the inner wall of the socket 30 do not interfere with the insertion of the liner 20 into the socket 30. That is, the liner 20, which is worn on the residual limb S, may be smoothly inserted into the hollow portion 31 of the socket 30.

To facilitate understanding, in FIG. 2, the residual limb S is illustrated in a state spaced apart from the liner 20, and the liner 20 is illustrated in a state spaced apart from the socket 30. However, in an actual state of use, the residual limb S is held in contact with the liner 20, and the liner 20 is held in contact with the socket 30. Particularly, when the liner 20 is inserted into the socket 30, the fibers of the fibrous pile fastener 40 on the outer surface of the liner 20 become intertwined with the fibers of the fibrous pile fastener 40 on the inner wall of the socket 30. These fibers become further intertwined as the user continues to move. As a result, the liner 20 and socket 30 further resist separation from each other.

As described above, the fibrous pile fasteners 40, each having a pile of fibers extending to incline toward the same direction, are applied to the liner 20 and the socket 30. This prevents the liner 20 is prevented from slipping off the residual limb S. Furthermore, the residual limb S, which is covered by the liner 20, is prevented from being separated from the socket 30. In this manner, a simple structure keeps the prosthesis 10 stably held on the residual limb S.

The fibers extending from each fibrous pile fastener 40 are inclined toward the same direction. Therefore, when an object that is in contact with the fibers moves in a direction that is reverse to the inclination direction of the fibers, the object raises the fibers. Accordingly, when a user who is using the prosthesis 10 moves his or her body, the residual limb S becomes further firmly fitted to the liner 20, and the liner 20 becomes further firmly fitted to the socket 30. Thus, in addition to stably holding the prosthesis 10 on the residual limb S, the present invention firmly attaches the prosthesis 10 to the residual limb S in conformance with the residual limb S.

Furthermore, each fibrous pile fastener 40 includes a pile of fibers. Thus, when the liner 20, which has the fibrous pile fastener 40 applied to its inner surface, is worn on the residual limb S, the inner surface does not adhere to the residual limb S. Consequently, unlike a silicon liner that would adhere to the residual limb S, the liner 20 prevents the residual limb S from becoming moist or irritated. Further, even though the liner 20 covers the residual limb S, the interior of the liner 20 is not sealed. Thus, air leakage that would produce unpleasant noise does not occur. This improves the comfort of the prosthesis 10.

The fibrous pile fastener 40, which may be applied to the liner 20 or the socket 30, includes fibers extending from a surface inclined toward the same direction. The fibers are inclined so as to restrict relative movement of an object when in contact with the object. More specifically, when the fibers are in contact with the object, the fibers produce a relatively small resistance acting in a first direction to enable smooth movement of the object in the first direction. Further, when the fibers are in contact with the object, the fibers produce a relatively large resistance acting in a second direction to restrict movement of the object in the second direction. When the fibrous pile fastener 40 is applied to the inner surface of the liner 20, the object would be the residual limb S. When the fibrous pile fastener 40 is applied to the outer surface of the liner 20, the object would be the socket 30. When the fibrous pile fastener 40 is applied to the inner wall of the socket 30, the object would be the liner 20.

It should be apparent to those skilled in the art that the present invention may be embodied in many other specific forms without departing from the spirit or scope of the invention. Particularly, it should be understood that the present invention may be embodied in the following forms.

For example, the fibrous pile fastener 40 does not have to be applied to both of the inner wall of the socket 30 and outer surface of the liner 20. The fibrous pile fastener 40 may be applied to just either one of the inner wall of the socket 30 and outer surface of the liner 20. In such a case, it is preferable that the other one of the inner wall of the socket 30 and the outer surface of the liner 20 have a roughened surface so that friction can be produced with the fibers of the fibrous pile fastener 40 to resist separation of the liner 20 and the socket 30. Additionally, instead of applying the fibrous pile fastener 40 to the liner 20, the liner 20 may be formed from a material having a pile of fibers from the beginning.

When arranging the fibrous pile fastener 40 on the inner wall of the socket 30, a pile of fibers may be formed on the surface of a rubber material containing bubbles, such as polychloroprene. Then, the rubber material may be applied to the inner wall of the socket 30. With such a structure, the rubber material arranged on the inner wall of the socket 30 elastically deforms in conformance with the shape of the user's residual limb S. This allows for the liner 20 to be reduced in thickness. Reduction in the thickness of the liner 20 enables easy fitting of the liner 20 onto the residual limb S and improves comfort when the liner 20 is worn on the residual limb S.

Moreover, by applying such a fibrous pile fastener 40, which is formed by forming a pile of fibers on a rubber material, to the inner wall of the socket 30, the liner 20 may be eliminated. In other words, the residual limb S may be directly inserted into the socket 30 without the liner 20. In this case, the fibers extending from the fibrous pile fastener 40 applied to the inner wall of the socket 30 are inclined toward the direction in which the residual limb S is inserted into the socket 30. Thus, the fibers of the fibrous pile fastener 40 on the inner wall of the socket 30 do not interfere with the insertion of the residual limb S into the socket 30, while preventing separation of the residual limb S from the socket 30.

The fibrous pile fasteners 40 do not necessarily have to be arranged on the closed lower portion of the liner 20 and portions of the socket 30 that do not come into contact with the liner 20 or the residual limb S. Furthermore, the advantages of the present invention may be obtained as long as the fibrous pile fastener 40 is arranged on part of at least one of the inner wall of the socket 30, the inner surface of the liner 20, and the outer surface of the liner 20.

An attachment may be used in lieu of the liner 20 and the socket 30 to attach the prosthesis 10 to the residual limb S. In this case, the fibrous pile fastener 40 may be arranged on the inner surface or outer surface of the attachment. When the fibrous pile faster 40 is arranged on the inner surface of the attachment, fibers extend from the inner surface of the attachment inclined toward a direction in which the residual limb S is inserted into the attachment. This prevents separation of the attachment from the residual limb S. When the fibrous pile faster 40 is arranged on the outer surface of the attachment, fibers extend from the outer surface of the attachment inclined toward a direction reversed from a direction in which the residual limb S is inserted into the attachment. This prevents separation of the attachment from the prosthesis 10.

Further, the fibers of the fibrous pile fastener 40 may extend from the inner surface or outer surface of the attachment in a direction inclined relative to a direction perpendicular to the axis of the attachment. The residual limb S is inserted into the attachment substantially along the axis of the attachment. When the fibers of the fibrous pile fastener 40 extend from the inner surface of the attachment in a direction inclined relative to the direction perpendicular to the axis of the attachment, the fibers restrict rotation of the attachment relative to the residual limb S. When the fibers of the fibrous pile fastener 40 extend from the outer surface of the attachment in a direction inclined relative to the direction perpendicular to the axis of the attachment, the fibers restrict rotation of the attachment relative to the prosthesis 10. The attachment may include at least either one of the liner 20 and the socket 30.

The present examples and embodiments are to be considered as illustrative and not restrictive, and the invention is not to be limited to the details given herein, but may be modified within the scope and equivalence of the appended claims.

What is claimed is:

1. A liner for use with a prosthesis, wherein the liner is adapted to receive a distal end of a residual limb, and the liner comprises:
    an inner surface, an outer surface, a proximal end, and a distal end; and
    a fibrous pile fastener from which a plurality of inclined fibers extend, wherein the fibrous pile faster is arranged on
        a) the inner surface of the liner, and the fibers are inclined toward the distal end of the liner to resist separation of the liner from the residual limb in a distal direction of the residual limb, and
        b) the outer surface of the liner, and the fibers are inclined toward the proximal end of the liner to resist separation of a socket of the prosthesis from the liner in the distal direction of the prosthesis.

2. A prosthesis for attachment to a residual limb, the prosthesis comprising:
    a liner, wherein a proximal end of the liner is adapted to receive a distal end of the residual limb, and the liner includes an inner surface and an outer surface; and
    a fibrous pile fastener from which a plurality of fibers extend, wherein the fibers extend from a surface of the liner and are generally linear throughout their length, the fibers are arranged on
        a) the inner surface of the liner, and the fibers are inclined toward the distal end of the liner to resist separation of the liner from the residual limb in a distal direction of the residual limb, and
        b) the outer surface of the liner, and the fibers are inclined toward the proximal end of the liner to resist separation of a socket of the prosthesis from the liner in a distal direction of the prosthesis.

3. A prosthesis for attachment to a distal end of a residual limb, the prosthesis comprising:
    a proximal end and a distal end;
    a socket, which is located at the proximal end of the prosthesis, wherein a proximal end of the socket is adapted to receive the distal end of the residual limb, and the socket includes an inner wall; and
    a socket fibrous pile fastener from which a plurality of fibers extend, wherein
        the socket fibrous pile fastener is arranged on the inner wall of the socket, and
        the fibers extending from the socket fibrous pile fastener on the inner wall of the socket are inclined toward a distal end of the socket,
    a liner, wherein
        the liner is adapted to fit between the distal end of the residual limb and the socket,
        the socket fibrous pile fastener comes into contact with the liner when the liner is fitted into the socket,
        the liner includes an inner surface and an outer surface, a proximal end, and a distal end, and,
        the socket fibrous pile fastener contacts the outer surface of the liner when the liner is fitted into the socket;
    an inner fibrous pile fastener from which a plurality of fibers extend, wherein
        the inner fibrous pile fastener is arranged on the inner surface of the liner, and
        the fibers extending from the inner fibrous pile fastener on the inner surface of the liner are inclined toward the distal end of the liner; and
    an outer fibrous pile fastener from which a plurality of fibers extend, wherein
        the outer fibrous pile fastener is arranged on the outer surface of the liner,
        the fibers extending from the outer fibrous pile fastener on the outer surface of the liner are inclined toward the proximal end of the liner, and
        the socket fibrous pile fastener contacts the liner with the outer fibrous pile fastener arranged between the liner and the socket when the liner is fitted into the socket.

4. A prosthesis for attachment to a distal end of a residual limb, the prosthesis comprising:
    a proximal end and a distal end;
    a socket, which is located at the proximal end of the prosthesis, wherein a proximal end of the socket is adapted to receive the distal end of the residual limb, and the socket includes an inner wall;
    a socket fibrous pile fastener from which a plurality of fibers extend, wherein
        the socket fibrous pile fastener is arranged on the inner wall of the socket;
        the fibers extending from the socket fibrous pile fastener on the inner wall of the socket are inclined toward a distal end of the socket, and
        the fibers are generally linear throughout their length; a liner, wherein
        the liner is adapted to fit between the distal end of the residual limb and the socket, and
        the socket fibrous pile fastener comes into contact with the liner when the liner is fitted into the socket, and
        the liner includes an outer surface, a distal end, and a proximal end; and
    an outer fibrous pile fastener from which a plurality of fibers extend, wherein
        the outer fibrous pile fastener is arranged on the outer surface of the liner,
        the fibers extending from the outer fibrous pile fastener on the outer surface of the liner are inclined toward the proximal end of the liner, and
        the socket fibrous pile fastener comes into contact with the liner with the outer fibrous pile fastener arranged between the liner and the socket when the liner is fitted into the socket.

* * * * *

UNITED STATES PATENT AND TRADEMARK OFFICE
CERTIFICATE OF CORRECTION

| | | |
|---|---|---|
| PATENT NO. | : 8,142,517 B2 | Page 1 of 1 |
| APPLICATION NO. | : 12/497117 | |
| DATED | : March 27, 2012 | |
| INVENTOR(S) | : Kota Horie | |

It is certified that error appears in the above-identified patent and that said Letters Patent is hereby corrected as shown below:

IN THE CLAIMS:

In column 7, line 15, in Claim 1, delete "faster" and insert -- fastener --, therefor.

In column 8, line 4, in Claim 3, delete "and," and insert -- and --, therefor.

In column 8, lines 38-39, in Claim 4, delete "a liner, wherein" and insert the same below "length;" on Col. 8, Line 39 as a new line.

Signed and Sealed this
Fourth Day of December, 2012

David J. Kappos
*Director of the United States Patent and Trademark Office*